(12) United States Patent
Talmer et al.

(10) Patent No.: US 9,383,296 B2
(45) Date of Patent: Jul. 5, 2016

(54) REAGENT CONTAINER PACK

(71) Applicant: Biokit, S.A., Barcelona (ES)

(72) Inventors: Mark Talmer, Pepperell, MA (US);
Robert C. Aviles, Merrimack, NH (US);
Luis Miguel Garcia Gros, Barcelona (ES); Paul C. Dahlstrom, Hollis, NH (US); Derek Verhoorn, Chelmsford, MA (US); Dan O'Sullivan, Mount Vernon, NH (US)

(73) Assignee: Biokit, S.A. (ES)

( * ) Notice: Subject to any disclaimer, the term of this patent is extended or adjusted under 35 U.S.C. 154(b) by 33 days.

(21) Appl. No.: 14/246,220

(22) Filed: Apr. 7, 2014

(65) Prior Publication Data
US 2014/0287525 A1   Sep. 25, 2014

Related U.S. Application Data (60) Division of application No. 12/271,635, filed on Nov. 14, 2008, now Pat. No. 8,728,413, which is a continuation-in-part of application No. 11/704,001, filed on Feb. 8, 2007, now Pat. No. 7,731,414.

(51) Int. Cl.
| | |
|---|---|
| *G01N 35/00* | (2006.01) |
| *G01N 1/28* | (2006.01) |
| *B01F 11/00* | (2006.01) |
| *B01F 15/00* | (2006.01) |
| *G01N 35/04* | (2006.01) |
| *G01N 35/02* | (2006.01) |

(52) U.S. Cl.
CPC ............ *G01N 1/286* (2013.01); *B01F 11/0002* (2013.01); *B01F 11/0005* (2013.01); *B01F 15/00915* (2013.01); *G01N 35/04* (2013.01); *G01N 35/0098* (2013.01); *G01N 35/026* (2013.01); *G01N 2035/0405* (2013.01); *Y10T 436/2575* (2015.01)

(58) Field of Classification Search
CPC .. G01N 1/28; G01N 21/07; G01N 2021/0375
USPC .................................. 236/45, 43; 436/45, 43
See application file for complete search history.

(56) References Cited

U.S. PATENT DOCUMENTS

| | | |
|---|---|---|
| 4,259,289 A | 3/1981 | Curry et al. |
| 5,221,519 A | 6/1993 | Wuerschum |
| 5,540,890 A | 7/1996 | Clark et al. |
| 5,542,575 A | 8/1996 | Stark et al. |
| 5,594,164 A | 1/1997 | Bull |
| 5,599,501 A | 2/1997 | Carey et al. |
| 5,632,399 A | 5/1997 | Palmieri et al. |
| 5,885,529 A | 3/1999 | Babson et al. |
| 5,888,835 A | 3/1999 | Bushnell et al. |
| 5,985,671 A | 11/1999 | Leistner et al. |
| 6,048,496 A | 4/2000 | Zhou et al. |
| 6,149,872 A | 11/2000 | Mack et al. |
| 6,413,420 B1 | 7/2002 | Foy et al. |
| 6,562,239 B2 | 5/2003 | Foy et al. |
| 7,731,414 B2 | 6/2010 | Vincent et al. |
| D620,603 S | 7/2010 | Talmer et al. |
| 8,550,697 B2 | 10/2013 | Vincent et al. |
| 2003/0215364 A1* | 11/2003 | Aviles .................. G01N 35/025 422/63 |
| 2007/0077646 A1 | 4/2007 | Okamoto |
| 2008/0085215 A1 | 4/2008 | Mototsu et al. |
| 2008/0192567 A1 | 8/2008 | Vincent et al. |
| 2009/0129988 A1 | 5/2009 | Talmer et al. |
| 2014/0086005 A1 | 3/2014 | Vincent et al. |

FOREIGN PATENT DOCUMENTS

| | | |
|---|---|---|
| EP | 0523425 | 1/1993 |
| EP | 0632271 | 1/1995 |
| EP | 0712000 | 5/1996 |
| EP | 0806665 | 11/1997 |
| EP | 0889328 | 1/1999 |
| WO | WO 98/18008 | 4/1998 |
| WO | WO 99/18481 | 4/1999 |
| WO | WO 02/37078 | 5/2002 |
| WO | WO 03/020427 | 3/2003 |

\* cited by examiner

*Primary Examiner* — Natalia Levkovich
(74) *Attorney, Agent, or Firm* — Burns & Levinson, LLP (57) ABSTRACT

A reagent container pack for storing, preserving, and automatically unsealing and resealing a plurality of reagent containers in a reagent container pack on-board an automated clinical sample analyzer for analyzing analytes in a body fluid.

11 Claims, 6 Drawing Sheets

REAGENT CONTAINER PACK

CROSS-REFERENCE TO RELATED APPLICATIONS

This application is a divisional application of a continuation-in-part application Ser. No. 12/271,635, filed on Nov. 14, 2008, which is a continuation-in-part application claiming priority to and the benefit of U.S. patent application Ser. No. 11/704,001, filed on Feb. 8, 2007, now granted U.S. Pat. No. 7,731,414, the contents of each of which in their entirety are incorporated by reference herein.

TECHNICAL FIELD OF THE INVENTION

The present invention relates to an automated clinical sample analyzer and more specifically to a reagent container pack for preserving, storing, and providing access to reagents for use by the automated clinical sample analyzer.

BACKGROUND

Automatic clinical sample analyzers are common in hospitals and research institutions for analyzing large quantities of samples. For example, environmental specimens, such as water, or patient specimens, such as blood, urine or other biological samples, can be tested using automated sample analyzers to determine concentrations of contaminants err analytes, for example.

Automated clinical sample analyzers have a variety of component systems that work in concert to manipulate patient samples. For example, an automated clinical sample analyzer may have one or more reagent dispensing components, sample holder dispensing components, sample and reagent probes, washing stations, detecting mechanisms, and automated arms, carousels, or conveyors for moving samples from one station to another.

Automated clinical sample analyzers reduce time taken to perform assays on patient samples, improve output, and reduce human error and contamination, thereby providing cost effective sample analysis. However, despite the automated functioning of such analyzers, operator intervention is often required if a component malfunctions, or if consumables, such as reagents and sample holders, need replacing. Therefore, there is a need in the art for an automated clinical sample analyzer that reduces the need for operator intervention, thereby further improving efficiency, accuracy of testing, and throughput.

In satisfaction of the above-mentioned needs and others, the present teachings relate to a system for providing a plurality of reagents in a single reagent container pack that can be stored, preserved and readily accessed onboard an automated clinical sample analyzer for detecting or measuring one or more analytes in a body fluid.

SUMMARY OF THE INVENTION

In one aspect, the invention relates to an automated clinical sample analyzer for analyzing patient samples. In one embodiment of the invention, the analyzer includes a reagent container pack for storing, preserving, and reducing evaporation of reagents, automatically unsealing and resealing reagent containers, and minimizing contamination of reagent containers in the reagent pack by reducing operation intervention.

In one embodiment, the reagent container pack includes a housing or base for holding a plurality of reagent containers. The base includes a bottom, back wall and a vertical slot in the back wall extending from the bottom of the base along a portion of the back wall.

The reagent container pack has a cover. The cover fits over the top and partially down the sides of the reagent container pack and is translatable from an elevated position above the reagent containers to a lower position in contact with the tops of the reagent containers. The cover includes a horizontal slot near the cover surface extending from one end to the other end of the cover. The cover further includes a plurality of holes in the cover surface in communication with hollow tubes projecting from the surface of the cover towards the tops of the reagent containers. Each of the hollow tubes has an opening into the hollow tube at each end. In one embodiment, the end of each hollow tube on the reagent container side of the cover includes a tip.

The reagent container pack includes a lid which has a plurality of through-holes corresponding in number to the hollow tubes of the cover. The lid is horizontally and reversibly slideable in the horizontal slot of the cover such that in one position the lid covers each of the hollow tubes and in another position the lid is uncovered from each of the hollow tubes of the cover.

An elongated tab is joined at one end to a fixed end of the cover at a hinge and extends downward along the back of the cover toward the base bottom. The other end of the elongated tab is secured to and slideably moveable in the vertical slot along the back side of the base. The inner surface of the elongated tab includes a horizontal tab projecting from the elongated tab towards the back of the base. When the upper portion of elongated tab, i.e., the portion above the horizontal tab, is pushed or pulled toward the back of the base, the lid transitions from a relaxed position in which the lid covers or "closes" the hollow tubes of the cover, to a biased position in which the hollow tubes of the cover are uncovered or "open". When the cover is in the lower position over the tops of the reagent containers, the transitioning of the lid from closed to open also uncovers the openings at the top of the reagent containers so that reagents can be accessed by, for example, a pipette.

When the push or pull on the elongated tab is released, the lid returns to its relaxed position from the biased position. In the relaxed position, the holes in the lid are not aligned with the hollow tubes of the cover and the holes in the cover surface thereby sealing the openings of the reagent containers contained within the pack.

In another aspect, the invention relates to a method for storing, preserving, and automatically unsealing and resealing reagent containers in a reagent pack on-board an automated clinical sample analyzer by the components of the reagent container pack described herein.

BRIEF DESCRIPTION OF THE FIGURES

These embodiments and other aspects of this invention will be readily apparent from the detailed description below and the appended drawings, which are meant to illustrate and not to limit the invention, and in which.

DESCRIPTION OF THE INVENTION

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

Embodiments of the invention relate to an automated clinical sample analyzer system for the automated analysis of patient samples. In one embodiment, the analyzer may be used to analyze target biomolecules in bodily fluid samples, such as blood, plasma, serum, urine, or cerebrospinal fluid. The automated clinical sample analyzer system according to the invention includes automation of immunochemical assays for the detection of a target biomolecule, for example, in a patient sample.

Embodiments of the present invention relate to an apparatus and method for preserving, storing and providing access to reagents in an automated clinical sample analyzer for the detection and/or measurement of target analytes in a body fluid sample. The present invention is advantageous over prior art automated clinical sample analyzers at least by minimizing manual operator interface with reagents by automating disruption of reagent container seals and automating preservation, reducing evaporation, and minimizing contamination of reagents by automated unsealing and resealing of the reagent containers without operator intervention.

Figure 1A:
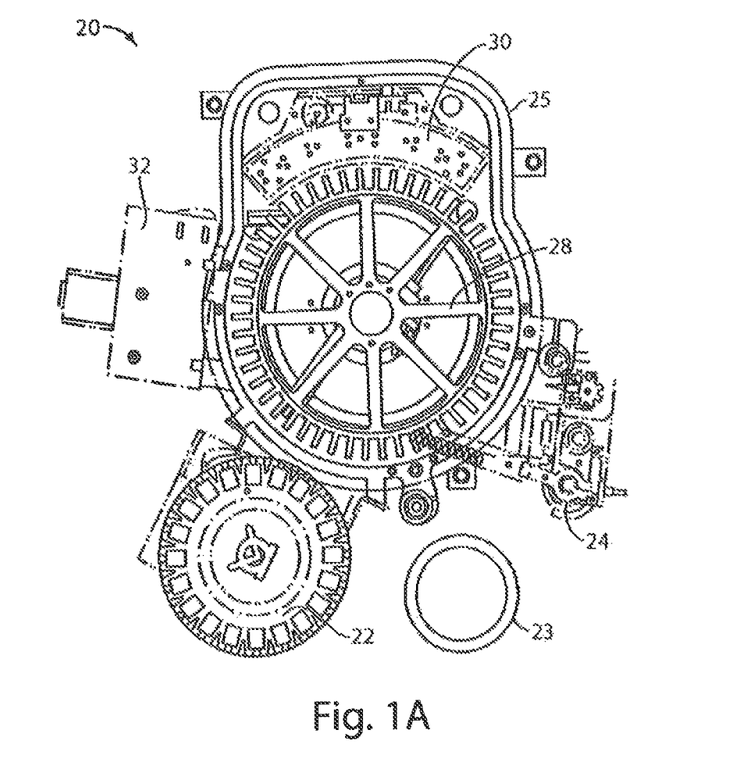
FIG. 1A is a top view of the automated clinical sample analyzer system. according to an exemplary embodiment of the present invention.

FIG. 1A is a top view of an automated clinical sample analyzer system 20 according to an embodiment of the present invention. The illustrated automated clinical sample analyzer system 20 contains one or more stations or modules for treatment and analysis of patient samples contained in a vial. In one embodiment, the automated clinical sample analyzer system 20 includes at least the following: a vial loader 22, a sample station (not shown) for adding a sample into a vial, a reagent station 23 for holding reagents for use in a diagnostic assay, a plurality of pipettes 24 for providing wash and rinse fluid to the vial, and for transporting reagents and samples into vials, a carousel 28 for receiving vials from the vial loader and distributing the vials, a magnetic washing module 30, a luminometer 32, and a heater module 25 to incubate the sample vial.

Figure 1B:
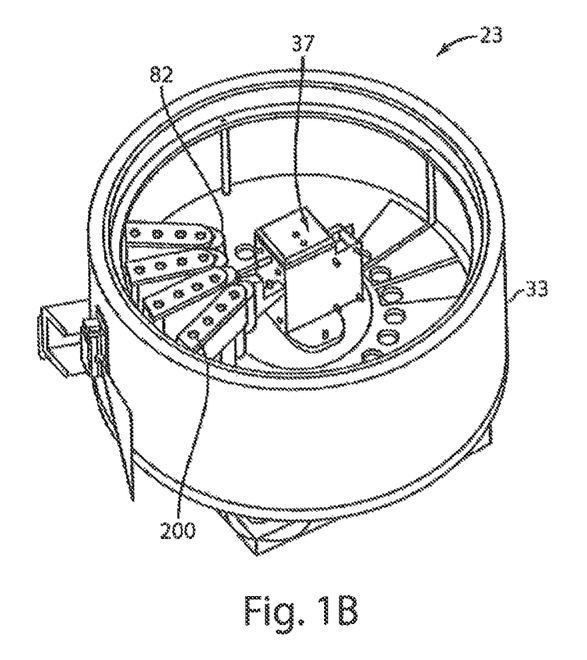
FIG. 1B is a perspective view of the reagent station according to an exemplary embodiment of the present invention.

FIG. 1B is a perspective view of the reagent station 23 according to an exemplary embodiment of the invention. The reagent station 23 includes a reagent station housing 33, a bar code scanner 37 and one or more reagent container packs 200, wherein each reagent container pack has a bar code 82. The reagent station housing 33 may be, for example, a bowl shaped container made of cast metal or plastic. One or more reagent container packs 200 are stored within the reagent station bowl 33. For example, the reagent container pack 200 may be radially distributed from the center of the bowl-shaped housing 33. In one embodiment, the reagent container pack 200 is inserted in a rotation carousel (not shown) positioned in the housing. The reagent station 23 may be temperature and/or humidity controlled.

A reagent container pack 200 contains reagents in reagent containers 208 which may be injected from the reagent container into a vial. In one embodiment, the reagent container pack 200 is wedge or pie shaped such that a plurality of reagent container packs 200 may fit into the round or bowl-shaped reagent station housing 33. For example, 5 to 35 reagent container packs 200, or more specifically, 10, 20 or 30, or more reagent container packs 200 may be placed into the reagent station housing 33 at one time, depending on the size of the reagent station housing 33.

With continued reference to FIG. 1B, the bar code scanner 37 permits a user to index and track the various reagent container packs 200. The bar code scanner 37 may read a bar code 82 placed on the side of the reagent container pack 200 facing the bar code scanner 37. The bar code reading is sent to a computer processor that alerts the user of the automated clinical sample analyzer system 20 of the location and content of the various reagent container packs 200. Additionally, the bar code scanner 37 permits the user to electronically select various reagent container packs 200 for the desired analysis. The user may request required reagents and the bar code scanner 37 identifies the corresponding reagent container pack 200 containing those reagents. Thus, the bar code label 82 may be used to distinguish between different reagents in the reagent container packs 200 and may assist a user to determine the location of certain reagents within the reagent station 23.

Figure 2:
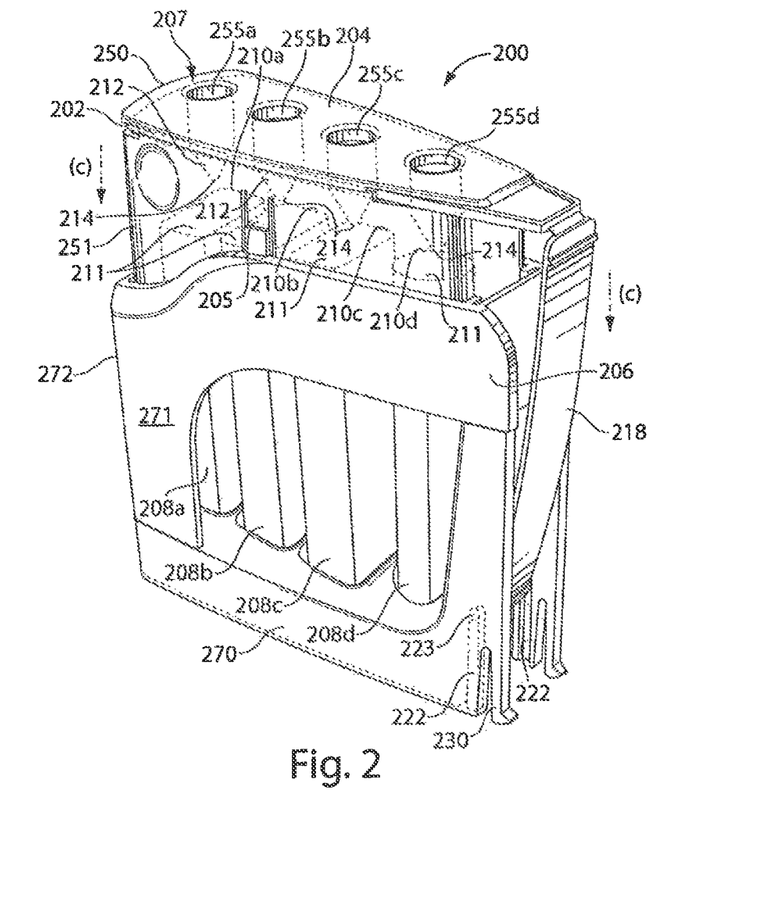
FIG. 2 is a perspective side-view of a reagent container pack including sealed reagent containers and a cover in an elevated position according to an exemplary embodiment of the invention.

FIG. 2 illustrates a reagent container pack 200 according to an exemplary embodiment of the invention. The reagent container pack 200 includes a self-sealing lid 202, cover 204, elongated tab 218, and a base 206 for housing a plurality of reagent containers 208, e.g., reagent tubes. The base 206 has a bottom 270. The bottom 270 may have a plurality of openings for engaging reagent containers 208. In one embodiment, the base has a back side 230, front side 272, and two side walls 271. The cover 204 is vertically translatable relative to the base 206 as shown by direction arrow "C". The self-sealing lid 202 is positioned in a horizontal slot 217 between the top portion 250 of the cover 204 and the bottom portion 251 of the cover. The top portion of the cover 250 has a plurality of holes 255a, b, c, d. In one embodiment, the top portion 250 of the cover 204 is optional and the self-sealing lid 202 is positioned on the surface of the cover portion 250.

FIG. 2 illustrates four reagent containers, 208a, 208b, 208c and 208d, housed within the reagent pack 200. However the invention is not limited to the number of reagent containers illustrated and may have two, three, five or more reagent containers in a reagent container pack 200. Reagent containers 208 hold a reagent, e.g., an antibody solution, buffer, or visualant, for example.

The reagent container pack 200 can have any convenient geometric shape, for example, a wedge-like shape, as illustrated in FIG. 1B, which allows a plurality of such reagent "wedges" to be placed side-by-side in a pie-like configuration on a carousel of an automated clinical analyzer, thereby permitting a wide variety of reagents types to be accessible for clinical analytical operations. Alternatively, the reagent container packs can be positioned in a linear or side-by-side array to provide a box-shaped configuration (not shown) in an automated clinical sample analyzer.

According to one embodiment of the invention, the reagent containers 208 are removable and pre-filled with selected reagents. Each of the reagent containers 208a, 208b, 208c, and 208d, for example, include an opening 210a, 210b, 210c, and 210d, respectively, at the top of the reagent container. In one embodiment, the openings are pre-sealed with a seal 211 such as a piercable, adhesive-coated, metallic foil seal.

Figure 3A:
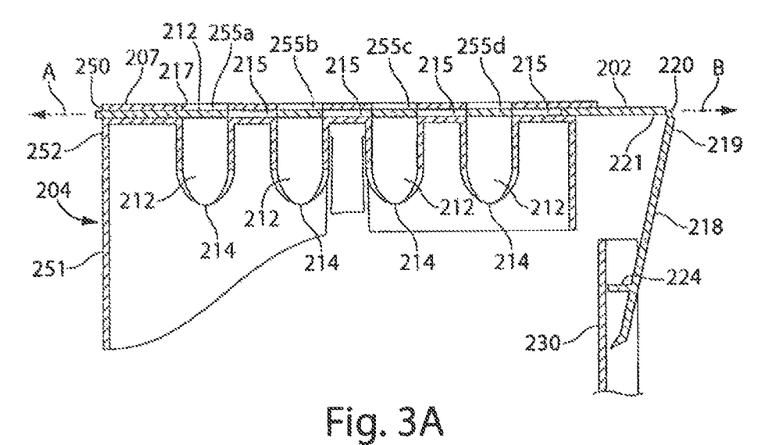
FIG. 3A is a cross-sectional view of the cover and lid of the reagent container pack illustrated in FIG. 2 with the lid positioned over the openings of the hollow tubes of the cover according to an exemplary embodiment of the invention.
Figure 3B:
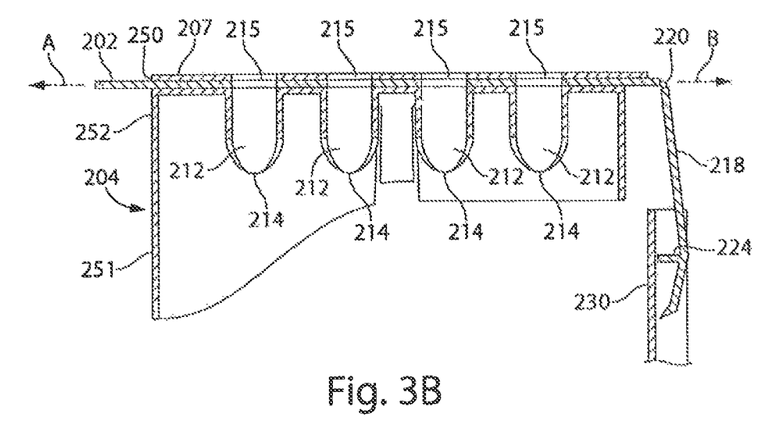
FIG. 3B is a cross-sectional view of the cover and lid illustrated in FIG. 3A with the openings of the hollow tubes uncovered by the lid according to an exemplary embodiment of the invention.

In one embodiment of the invention, each of the openings 210a, 210b, 210c, and 210d of the reagent containers 208a, 208b, 208c, and 208d, respectively, share a common cover 204. Referring to FIGS. 3A and 3B, the cover 204 includes a device for opening the seals 211 affixed to the tops 210a, 210b, 210c, and 210d of the reagent containers. For example, in one embodiment, the cover 204 includes a hollow piercing tube device 212 for piercing the seals 211 affixed over each of the openings 210a, 210b, 210c, and 210d of the reagent containers. According to one embodiment, the hollow piercing tubes 212 extend from the top surface 207 of the cover 204 toward the openings 210a, 210b, 210c, and 210d at the top of the reagent containers. According to another embodiment, the hollow piercing tubes 212 extend downward from the top surface 252 of the bottom portion 251 of the cover 204 toward the openings 210a, 210b, 210c, and 210d. of the tops of the reagent containers 208.

Referring to FIG. 2, in one embodiment, each of the hollow piercing tubes 212 includes a tip 214. The tip 214 is capable of piercing the seals 211 on the reagent containers 210 when the cover 204 is pushed down in the direction of Arrow "C" from an elevated position shown in FIG. 2 over the top of the reagent containers 208a, 208b, 208c, and 208d to a lower position shown in FIG. 4 closer to the tops of the reagent containers 208a, 208b, 208c, and 208d.

Referring again to FIG. 2, in one embodiment according to the invention the cover 204 includes at least one snap lock mechanism 205 placed on the side of the cover 204. In one embodiment, the snap lock mechanism must be compressed inwardly to permit the cover 204 to transition downward toward the bottom of the base in the direction of arrow "C" from the elevated position illustrated in FIG. 2 to the lower position illustrated in FIG. 4. In one embodiment, a snap lock mechanism 205 is placed on each side of the cover 204.

After the seals 211 are pierced, the self-sealing lid 202 automatically reseals the reagent containers 208a, 208b, 208c, and 208d between intermittent reagent extractions without the need for external manipulation to effect re-closure.

Figure 5:
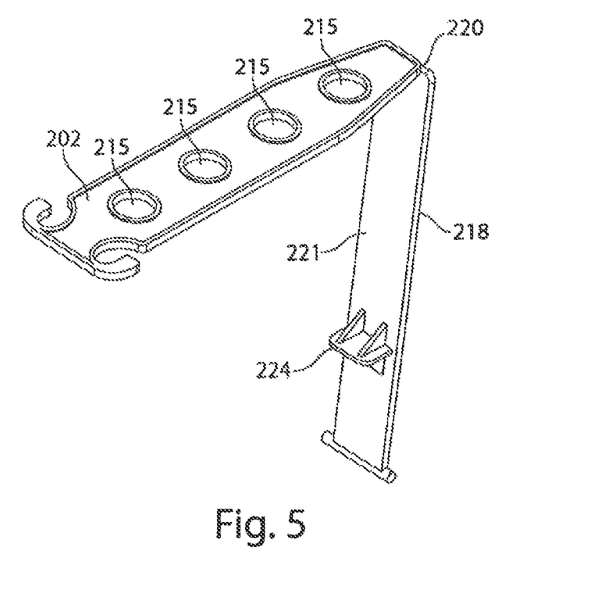
FIG. 5 is a top perspective view of the sealing lid joined to the elongated tab according to one embodiment of the invention.

Referring to FIG. 5, in one embodiment of the invention, the sealing lid 202 is a planar, substantially rectangular, molded plastic member including a plurality of through-openings 215 in the lid 202 which correspond in number and distribution to the hollow piercing tubes 212 in the cover 204 and to the openings 210a, 210b, 210c, and 210d at the top of each reagent container 208a, 208b, 208c and 208d, respectively. The plurality of openings 215 in the lid 202 also correspond in number to the number of holes 255 in the top portion 250 of the cover 204.

Referring again to FIG. 3A, the sealing lid 202 is reversibly slideably moveable in a horizontal direction in the direction of arrows "A" and "B" in a horizontally oriented slot 217 positioned at the top of the cover 204. One end of the sealing lid 202 is joined to one end 219 of an elongated tab 218 by a hinge 220, for example, a plastic hinge that can be molded in the elongated tab 218 or the sealing lid when these elements are manufactured. For example, the plastic hinge 220 is part of one integrally molded piece which includes the elongated tab 218, the sealing lid 202 and the hinge 220.

Figure 4:
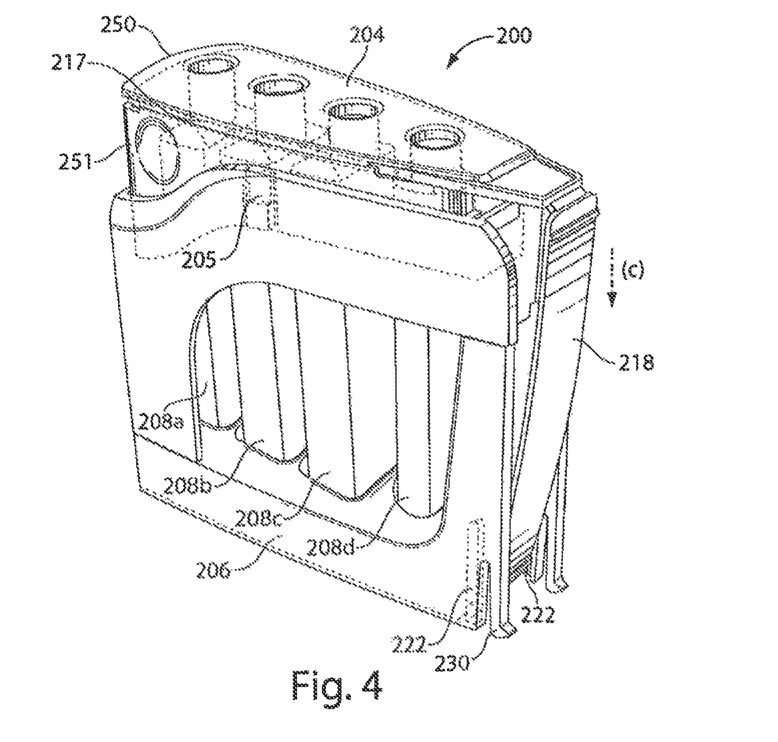
FIG. 4 is a perspective side-view of the reagent container pack illustrated in FIG. 2 with the cover in the lower position with the seals of the reagent containers broken by the hollow tubes according to an exemplary embodiment of the invention.

Referring again to FIG. 2, the elongated tab 218 extends downward toward the bottom of the base 206 from the hinge 220. The other end 223 of the elongate tab 218 is secured and slideably moveable in a slot 222 located along the back side 230 of the base 206 of the reagent container pack 200. The slot 222 extends from the bottom of the base 206 along a portion of the back wall 230 toward the top of the base. Accordingly, downward pressure on the elongated tab 218, caused by, for example, downward pressure on the cover 204 as illustrated in FIG. 4, moves the end 223 of the elongated tab 218 downward in the slot 222. Referring to FIG. 4, this freedom of movement of the elongated tab 218 in a vertical downward direction allows the elongated tab 218 to slide down in the slot 222 as the cover 204 is pushed onto the top of the reagent containers 208 to pierce the seals 211 with the hollow piercing tubes 212.

Referring to FIG. 5, at a position about one third the distance from the secured lower end 223 of the elongated tab 218, a horizontal tab 224 projects horizontally from the inner face 221 of the elongated tab 218 towards the back 230 of the base 206. Referring to FIG. 3A, when the upper two-thirds of the tab 218 that is the portion of the tab 218 above horizontal tab 224 is translated in the direction of arrow "A", the lid 202 moves in the same direction as arrow "A" allowing the holes 215 in the sealing lid 202 to "open" by alignment of the holes 215 with the piercing tubes 212 and the openings 250 at the top portion 250 of the cover 204.

Referring to FIG. 3B, spring bias is generated by the horizontal tab 224 being forced against the back portion 230 of the base 206 and applying pressure to the elongated tab 218 above the horizontal tab 224. When the pressure on the elongated tab 218 is released and the horizontal tab 224 is no longer forced against the back portion 230, the elongated tab 218 is biased back to its original relaxed position illustrated in FIG. 3A and the sealing lid 202 closes the openings 255 in the cover 204 and covers the openings of the piercing tubes 212 when it translates in direction of arrow "B" thereby returning to its original position. In the relaxed position, the holes of the sealing lid 215 are no longer aligned with the piercing tubes 212, the openings 250 of the cover 204 and the openings 210 of the reagent containers 208. Consequently, the openings 210 of the reagent containers 206 are "closed."

The reagent wedges, i.e., reagent container packs, of the invention will simultaneously support a relatively large number of assay types, e.g., up to 30 or more, each requiring up to 2 or more reagents, without reduction of the on-board assay capacity of an automated clinical chemical, biochemical, or immunoassay analyzer. The reagent container packs of the invention also provide the ability to store, preserve and access reagents on-board a immunoanalyzer, for example, for relatively extended periods of time, without detectable degradation. The reagent packs of the invention also permit reagents to be positively identified via an attached bar code.

A rotating carousel described herein accommodates a plurality of wedge-shaped reagent packs, each reagent pack capable of holding a plurality of different reagents in different compartments thereof. These packs include instrument actuated covers with seal piercing devices as well as bar codes which are accessible to the bar code reader. In one embodiment, the entire carousel is housed within a refrigerator chamber maintained at about 4° C.

By way of illustration, the reagents contained in the reagent containers are supplied in liquid form, and are used to generate a detectable signal proportional or inversely proportional to the concentration of analyte in a specimen. Reagents are contained within reagent container packs in disposable reagent container packs, each bearing a plurality, e.g., up to two or more, different reagents. These reagent container packs protect their contents from the environment by virtue of their instrument actuated lids.

A plurality, e.g., up to 24 or more, of different reagent packs can be simultaneously mounted on the automated clinical scope analyzer, and the operator may replace or supplement the supply of packs at any time. A quantity of reagent may be consumed from one or more of the containers of a reagent pack for each test conducted by insertion of an aspiration by, for example, a pipette.

What is claimed is:

1. A method for obtaining a reagent comprising:
    providing a reagent container pack comprising a plurality of reagent containers, each of said plurality of reagent containers comprising a seal and containing at least one reagent, said reagent container pack further comprising,
    a base for holding a plurality of reagent containers, said base comprising a bottom, a back wall, and a vertical slot extending from the bottom of said base along a portion of the back wall of said base,
    a cover comprising a top, a horizontal slot extending from one end of the cover to the other end of the cover and a plurality of hollow tubes joined to said cover, said tubes comprising a first end and a second end, each of said first and second ends comprising an opening,
    a lid comprising a plurality of holes, a free end, and a fixed end, wherein said lid is horizontally and reversibly slideable in the horizontal slot of the cover, and
    an elongated tab fixed at one end to said fixed end of said lid;
    translating said cover vertically relative to said base;
    piercing the seal on said reagent container contained within the base;
    applying a biasing force to the elongated tab to transition said lid from a first relaxed position to a second biased position;
    inserting a pipette into one of said plurality of reagent containers via an opening in said lid;
    aspirating said at least one reagent into said pipette; and
    releasing said biasing force on said elongated tab.

2. The method of claim 1 wherein said at least one reagent is a liquid.

3. The method of claim 1 wherein said translation of said cover further comprises moving said cover from an elevated position above said reagent container to a lower position in contact with the top of said reagent container.

4. The method of claim 1 wherein said relaxed position of said lid comprises a closed lid and wherein said biased position comprises an open lid.

5. The method of claim 4 further comprising piercing said seal on the reagent containers before aspirating said at least one reagent.

6. The method of claim 5 wherein said at least one reagent is aspirated from the top of the reagent container.

7. The method of claim 1 wherein said plurality of reagent containers is pre-filled with selected reagents.

8. The method of claim 1 wherein each of said plurality of reagent containers is removable.

9. The method of claim 1 wherein said at least one reagent is selected from the group consisting of an antibody solution, a buffer, and a visualant.

10. The method of claim 1 wherein each of said at least one reagent in said plurality of reagent containers is identified by a bar code.

11. A method for obtaining a reagent comprising:
    providing a reagent container pack comprising a plurality of reagent containers, each of said plurality of reagent containers comprising a seal and containing at least one reagent, wherein said plurality of reagent containers are pre-filled with selected reagents, said reagent container pack further comprising,
    a base for holding a plurality of reagent containers, said base comprising a bottom, a back wall, and a vertical slot extending from the bottom of said base along a portion of the back wall of said base,
    a cover comprising a top, a horizontal slot extending from one end of the cover to the other end of the cover and a plurality of hollow tubes joined to said cover, said tubes comprising a first end and a second end, each of said first and second ends comprising an opening,
    a lid comprising a plurality of holes, a free end, and a fixed end, wherein said lid is horizontally and reversibly slideable in the horizontal slot of the cover, and an elongated tab fixed at one end to said fixed end of said lid;
    translating said cover vertically relative to said base;
    piercing the seal on said reagent container contained within the base before aspirating said at least one reagent;
    applying a biasing force to the elongated tab to transition said lid from a first relaxed position to a second biased position wherein the relaxed position of said lid comprises closing the lid and wherein the biased position of said lid comprises opening the lid;
    inserting a pipette into one of said plurality of reagent containers via an opening in said lid;
    aspirating said at least one reagent into said pipette; and
    releasing said biasing force on said elongated tab.

* * * * *